US012582751B2

(12) United States Patent
Degen et al.

(10) Patent No.: US 12,582,751 B2
(45) Date of Patent: Mar. 24, 2026

(54) SEALING MATERIAL FOR A MEDICAL IMPLANT

(71) Applicant: CORTRONIK GMBH, Rostock (DE)

(72) Inventors: Nicolas Degen, Beringen (CH); Sebastian Kaule, Rostock (DE); Sabine Illner, Rostock (DE); Stefanie Kohse, Rostock (DE); Niels Grabow, Rostock (DE); Klaus-Peter Schmitz, Rostock (DE)

(73) Assignee: CORTRONIK GMBH, Rostock-Warnemünde (DE)

( * ) Notice: Subject to any disclaimer, the term of this patent is extended or adjusted under 35 U.S.C. 154(b) by 801 days.

(21) Appl. No.: 17/768,321

(22) PCT Filed: Oct. 7, 2020

(86) PCT No.: PCT/EP2020/078121
§ 371 (c)(1),
(2) Date: Apr. 12, 2022

(87) PCT Pub. No.: WO2021/073978
PCT Pub. Date: Apr. 22, 2021

(65) Prior Publication Data
US 2023/0293773 A1     Sep. 21, 2023

(30) Foreign Application Priority Data

Oct. 17, 2019    (EP) .................................... 19203801

(51) Int. Cl.
*A61N 1/40*        (2006.01)
*A61L 27/40*       (2006.01)
*A61L 27/52*       (2006.01)

(52) U.S. Cl.
CPC ............... *A61L 27/40* (2013.01); *A61L 27/52* (2013.01); *A61L 2400/02* (2013.01)

(58) Field of Classification Search
CPC ......... A61L 27/40; A61L 27/52; A61N 1/406; A61K 9/5115; A61K 9/5192; A61K 47/02; A61K 47/6923; A61K 41/0052; A61P 35/00
See application file for complete search history.

(56) References Cited

U.S. PATENT DOCUMENTS

| | | | |
|---|---|---|---|
| 6,271,278 B1 | 8/2001 | Park et al. | |
| 2013/0150957 A1 | 6/2013 | Weber | |
| 2016/0194425 A1 | 7/2016 | Mitra et al. | |
| 2016/0355951 A1* | 12/2016 | Pham ........................ | D01F 1/10 |

FOREIGN PATENT DOCUMENTS

| | | | | |
|---|---|---|---|---|
| CA | 2610948 A1 * | 11/2006 | ............. | A61B 17/11 |
| NO | 137479 B * | 11/1977 | ....... | A61F 13/53752 |
| WO | 2013033791 A1 | 3/2013 | | |
| WO | 2015055652 A1 | 4/2015 | | |
| WO | 2017040851 A1 | 3/2017 | | |

OTHER PUBLICATIONS

Fast-degrading bioresorbable arterial vascular graft with high cellular infiltration inhibits calcification of the graft; Tadahisa Sugiura, et al.; J Vasc Surg.; 66(1):243-250; Jul. 2017 (Year: 2017).*
International Search Report from the corresponding International Patent Application No. PCT/EP2020/078121, dated Nov. 23, 2020.

* cited by examiner

*Primary Examiner* — Robert S Cabral
(74) *Attorney, Agent, or Firm* — Greer, Burns & Crain, Ltd.; Steven P. Fallon

(57)     ABSTRACT
A sealing material suitable for a medical implant. The material includes a composite structure of a first component, a second component and a third component. The first component includes at least one biologically inert polymer. The second component includes a hydrogel, which swells up after contact with an aqueous solution by a first volume increase within a first time period. The third component includes a hygroscopic matrix, which swells up after contact with an aqueous solution by a second volume increase within a second time period. The second time period is shorter than the first time period.

20 Claims, 10 Drawing Sheets

SEALING MATERIAL FOR A MEDICAL IMPLANT

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2020/078121, which was filed Oct. 7, 2020, which application claimed priority from European Application Serial Number 19203801.6, which was filed Oct. 7, 2019.

FIELD OF THE INVENTION

A field of the invention is sealing materials medical implants.

BACKGROUND

Various medical implants have the problem that after implantation a leak develops between the surface of the implant and an anatomical structure of the patient, for example a vessel wall, in which the implant was implanted. In the case of a heart valve prosthesis as medical implant, a paravalvular leak for example may occur, as a result of which the performance of the heart valve prosthesis is restricted. Conventional sealing materials have a number of disadvantages.

US Published Application No. 2017/0273786 A1 describes a medical implant having a sealing element which expands when a predefined temperature is exceeded. In order to achieve a uniform expansion in that case, the most uniform possible temperature distribution within the sealing element must be provided. This is usually only possible if the sealing element has a low wall thickness, which thus limits its maximum possible sealing function.

US Published Application No. 2013/0190857 A1 describes an endoluminal sealing element for sealing an endoluminal implant. Here, the sealing element expands when it is exposed to a liquid. To control the expansion process, the use of a semi-permeable membrane is provided here, through which a liquid can pass to the sealing material and can trigger expansion of the latter.

US Published Application No. 2016/0194425 A1 describes heavily expandable materials which can be used as sealing materials for medical implants. The sealing materials consist of a hydrogel which does not swell in a storage solution; after contact with an aqueous fluid, however, it swells within 15 minutes to between 200 and 1000 times its previous weight. The use of a semi-permeable membrane through which the aqueous fluid passes to the hydrogel is described.

US Published Application No. 2013/0150957 A1 describes a vessel valve system in which a hydrogel is provided which comprises a calcium-chelating agent and an acidifying agent. In particular, the focus here is on the treatment of calcified vessel valves, and not on a possible sealing by the hydrogel.

PCT Published Application WO 2015/055652 A1 describes a seal for a stent prosthesis. The seal has a hollow sleeve which defines a space for a first material which swells when it comes into contact with a constituent of a bodily liquid. In addition, the seal comprises a second material which is permeable at least for some constituents of the bodily liquid. Consequently, this international patent application also describes primarily the use of a semi-permeable membrane for absorbing a swellable material.

US Published Application No. 2017/0252155 A1 describes a heart valve prosthesis including a terminating material which, upon contact with blood, induces the formation of a thrombus which serves to seal off the heart valve prosthesis with respect to a vessel wall of a patient.

SUMMARY OF THE INVENTION

A preferred sealing material is suitable for a medical implant. The material includes a composite structure of a first component, a second component and a third component. The first component includes at least one biologically inert polymer. The second component includes a hydrogel, which swells up after contact with an aqueous solution by a first volume increase within a first time period. The third component includes a hygroscopic matrix, which swells up after contact with an aqueous solution by a second volume increase within a second time period. The second time period is shorter than the first time period.

BRIEF DESCRIPTION OF THE DRAWINGS

Further details of aspects of the present invention will be explained in greater detail hereinafter with reference to exemplary embodiments and figures. The figures show.

DETAILED DESCRIPTION OF THE PREFERRED EMBODIMENTS

Figure 1:
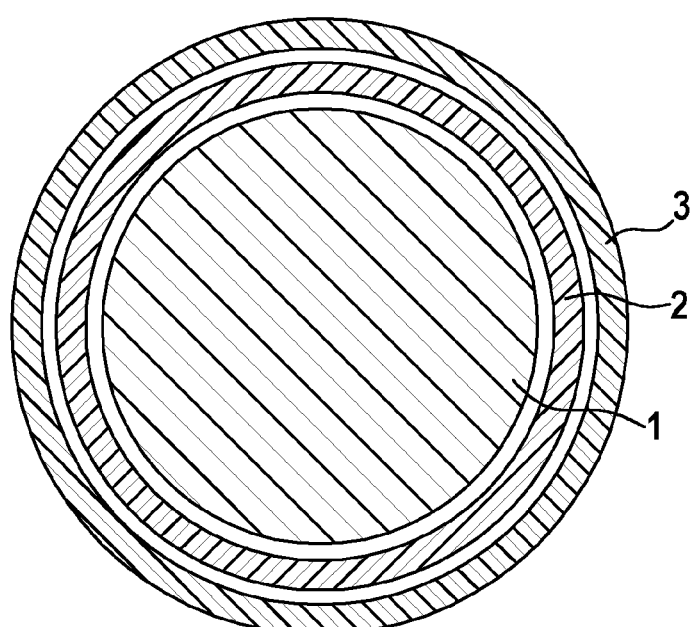
FIG. 1 a first exemplary embodiment of a thread formed from a sealing material.

A sealing material of the invention has a composite structure including a first component, a second component and a third component. The first component ensures a mechanical basic structure and a stability of the composite structure. The first component for this purpose includes at least one biologically inert polymer. In a variant, the first component consists of this biologically inert polymer. This biologically inert polymer is typically a biocompatible polymer; that is to say a polymer which itself, or the degradation products of which, is/are not toxic for an organism in which the sealing material is used, and which has no relevant negative influences on such an organism.

The second component is able to absorb a large amount of water going far beyond its own dry mass. The second component here has a mechanical stability at the same time. For this purpose, the second component includes a hydrogel, which swells up after contact with an aqueous solution and thus experiences a first volume increase within a first time period. This volume increase is typically also accompanied by an increase in the mass of the second component (specifically by the uptake of water). In a variant, the second component consists of this hydrogel.

The third component is also able to swell up. The swelling, however, occurs in this case within a shorter time period than the swelling of the second component. Consequently, the third component is a rapidly swelling substance. A mechanical stability of the third component is less relevant here. In accordance with the invention it is provided that the third component includes a hygroscopic matrix, which swells up after contact with an aqueous solution and thus experiences a second volume increase within a second time period. The rapidly swelling properties of the third component are defined in that the second time period is shorter than the first time period. In a variant, the third component consists of the hygroscopic matrix.

In the context of the present invention, the term "medical implant" in particular includes stent-based implants and heart valve prostheses, in particular aortic heart valve prostheses, which are stent-based. The term "medical implant" in accordance with the invention also infers any medical implant for which the sealing material is suitable for sealing the implant with respect to an anatomical structure.

Key advantageous effects result from the composite structure of the sealing material in accordance with the invention as compared to the sealing materials known from the prior art. For example, a mechanical stability of the sealing material is ensured at all times by the first component, specifically regardless of whether the sealing material is in its non-expanded or expanded (that is to say sealing) state. A two-stage swelling of the sealing material is achieved by an interaction between the second component and the third component. For example, the third component ensures a rapid swelling, which is supported by a slower swelling of the second component. Here, the rapid swelling of the third component already within the short second time period can ensure a tightness that for a short time period ensures a satisfactory function of a medical implant provided with the sealing material. Before this short time period expires, the second component then swells up and additionally also in its swollen state has a mechanical stability going beyond the mechanical stability of the third component. The sealing material can thus convey a permanent tightness and can thus ensure over a long time period a satisfactory function of a medical implant equipped with this sealing material.

Due to the two-stage swelling, it is thus ensured that a seal which is not long-lasting is provided rapidly (specifically by the third component) and a seal which is long-lasting is provided in a slightly delayed manner (specifically by the second component). Due to a seal that is constructed in multiple stages in this way, a sealing effect of the presently claimed sealing material that is improved as compared to the solutions known from the prior art is achieved. Here, the sealing material—when used to seal a medical implant—usually serves not only for sealing, but also for compensating for anatomical inconsistencies and consequently for filling undesired gaps/interstices between an anatomical structure and a medical implant on which the sealing material is arranged.

In a variant, the third component has a spongy structure. By a spongy structure of this kind, it is possible to compress the third component again following an expansion. This is then advantageous in particular if the sealing material is used on a medical implant. If, during the implantation process, it is found that, in spite of the swollen third component, the implant still does not seal properly with respect to an anatomical structure of a patient, for example a vessel wall, or that the implant is not positioned as desired, the implant must be frequently repositioned. For this purpose, the implant is retracted into a device that is used to implant the implant (so-called "resheathing"). For a retraction of this kind, however, the implant has to be compressed (crimped) again to a much smaller cross section that the cross section in which it is present in its expanded state. If the entire sealing material or a significant proportion thereof is already expanded, a retraction of this kind is no longer usually possible in the solutions known from the prior art. By contrast, the invention claimed herein, in particular in the variant in which the third component has a spongy structure, allows precisely such a retraction/resheathing since only the third component—and not the second component—initially expands. In other words, the time delay that results between the expansion of the third component and the expansion of the second component can be used to compress the third component again and to retract the entire implant. Following a repositioning, the implant can be transferred again into its expanded state. The third component then swells up again and—if the implant remains at the corrected implantation point—the second component also swells up. Consequently, there is permanently a good tightness between the medical implant and an anatomical structure of the patient, for example a vessel wall, which is provided by the sealing material claimed in accordance with the invention.

In a variant the first component or the at least one biologically inert polymer has a tensile strength of 0.1 $N/mm^2$ to 20 $N/mm^2$, in particular from 0.2 $N/mm^2$ to 19 $N/mm^2$, in particular from 0.5 $N/mm^2$ to 18 $N/mm^2$, in particular from 1 $N/mm^2$ to 17 $N/mm^2$, in particular from 2 $N/mm^2$ to 16 $N/mm^2$, in particular from 3 $N/mm^2$ to 15 $N/mm^2$, in particular from 4 $N/mm^2$ to 14 $N/mm^2$, in particular from 5 $mm^2$ to 13 $N/mm^2$, in particular from 6 $N/mm^2$ to 12 $N/mm^2$, in particular from 7 $N/mm^2$ to 11 $N/mm^2$, in particular from 8 $N/mm^2$ to 10 $N/mm^2$.

Alternatively or additionally, the first component or the biologically inert polymer in a variant has an elongation at break of 30% to 500%, in particular of 40% to 450%, in particular of 50% to 400%, in particular of 60% to 350%, in particular of 70% to 300%, in particular of 80% to 250%, in particular of 90% to 200%, in particular of 100% to 150%.

In a variant the second component or the hydrogel after the first volume increase has a tensile strength of 0.02 $N/mm^2$ to 1 $N/mm^2$, in particular of 0.05 $N/mm^2$ to 0.9 $N/mm^2$, in particular of 0.1 $N/mm^2$ to 0.8 $N/mm^2$, in particular of 0.2 $N/mm^2$ to 0.7 $N/mm^2$, in particular of 0.3 $N/mm^2$ to 0.6 $N/mm^2$, in particular of 0.4 $N/mm^2$ to 0.5 $N/mm^2$.

Alternatively or additionally, the second component or the hydrogel in a variant has an elongation at break of 30% to 130%, in particular of 40% to 120%, in particular of 50% to 110%, in particular of 60% to 100%, in particular of 70% to 90%.

In a variant the third component or the hygroscopic matrix after the second volume increase has a tensile strength of up to 2.5 $N/mm^2$, in particular of 0.001 $N/mm^2$ to 2.5 $N/mm^2$, in particular of 0.01 $N/mm^2$ to 2 $N/mm^2$, in particular of 0.1 $N/mm^2$ to 1.5 $N/mm^2$, in particular of 0.5 $N/mm^2$ to 1 $N/mm^2$.

Alternatively or additionally, the third component or the hygroscopic matrix in a variant has an elongation at break of 10% to 40%, in particular of 15% to 35%, in particular of 20% to 30%.

Here, the material for the third component or the hygroscopic matrix is typically selected in such a way that it has a lower mechanical stability than the material of the second component or the hydrogel.

In all of the aforementioned alternative embodiments, the tensile strength and the elongation at break are determined in accordance with ISO 527.

In a variant the first time period is 1 hour to 10 hours, in particular 1.5 hours to 9.5 hours, in particular 2 hours to 9 hours, in particular 2.5 hours to 8.5 hours, in particular 3 hours to 8 hours, in particular 3.5 hours to 7.5 hours, in particular 4 hours to 7 hours, in particular 4.5 hours to 6.5 hours, in particular 5 hours to 6 hours.

Alternatively or additionally, the first volume increase in a variant results in an increase of an initial volume of the hydrogel by at least a factor of 2. The first volume increase brings about in particular an increase of the initial volume of the hydrogen by a factor of from 2 to 1000, in particular of from 5 to 900, in particular of from 10 to 800, in particular of from 20 to 700, in particular of from 30 to 600, in particular of from 40 to 500, in particular of from 50 to 400, in particular of from 60 to 300, in particular of from 70 to 200, in particular of from 80 to 100. All of the above-mentioned time periods are combinable here with all of the above-mentioned volume increases.

A first time period of from 5 hours to 7 hours is particularly suitable. In addition, a volume increase by a factor of 20 to 60 is particularly suitable, wherein a combination of the above-mentioned particularly suitable intervals is likewise particularly suitable.

In a variant the second time period is 10 seconds to 59 minutes, in particular 15 seconds to 50 minutes, in particular 20 seconds to 40 minutes, in particular 30 seconds to 30 minutes, in particular 40 seconds to 20 minutes, in particular 50 seconds to 10 minutes, in particular 60 seconds to 5 minutes, in particular 90 seconds to 4 minutes, in particular 2 minutes to 3 minutes. A particularly suitable time period is 60 seconds to 120 seconds.

Alternatively or additionally, the second volume increase results in an increase of an initial volume of the hygroscopic matrix by at least a factor of 2. In particular the second volume increase brings about an increase of the initial volume of the hygroscopic matrix by a factor of from 2 to 1000, in particular of from 5 to 900, in particular of from 10 to 800, in particular of from 20 to 700, in particular of from 30 to 600, in particular of from 40 to 500, in particular of from 50 to 400, in particular of from 60 to 300, in particular of from 70 to 200, in particular of from 80 to 100. All of the above-mentioned time periods are combinable here with all of the above-mentioned volume increases.

In the context of the invention it is noted that the swelling behaviour of a hygroscopic matrix is typically dependent on the thickness/strength in which it is used. The thicker/stronger this layer, the more water can be bound in principle.

In a variant the hydrogel of the second component swells not only as the result of contact with an aqueous liquid. Rather, in this variant the hydrogel is such that an external stimulus ensures that the first volume increase is accelerated or increased (intensified). This external stimulus can be, for example, a temperature that is elevated as compared to a starting value, a pH value that is increased or reduced as compared to a starting value and/or an ion concentration that is increased or reduced as compared to a starting concentration. If the hydrogel responds to an external stimulus of this kind, the swelling properties of the hydrogel can additionally be influenced.

In a variant, the at least one biologically inert polymer is selected from the group consisting of polyurethanes, polyimides, polyethylenes, polypropylenes, polysulfones, polyesters, polytetrafluoroethylene, silicones, fluorosilicones, polyaryletherketones, polyvinylidene fluoride, vinylpyrrolidone/vinylacetate-copolymers and polyvinylfluoride.

In a variant the hydrogel includes at least one substance which is selected from the group consisting of polymerisable ionic liquids (ILs), thermosensitive polymers, polyacrylamides, polyoxazolines, polyvinylethers and polyethylene glycols. Vinylogous imidazolium-based ionic liquids, such as 1-vinyl-3-isopropylimidazolium bromide, are particularly suitable ionic liquids.

In a variant the hygroscopic matrix includes at least one substance which is selected from the group consisting of cellulose matrix, cellulose derivatives and chitosan.

In a variant the second component includes at least one substance for promoting endothelialisation. This may be an endothelial growth factor (VEGF). If a growth factor of this kind is integrated into the second component or the hydrogel, a very strong diffusion of the growth factor into the surrounding environment of the second component is achieved as the result of the strong swelling. If the sealing material is arranged for example on a heart valve prosthesis as medical implant, it is thus possible to achieve a strong diffusion of a growth factor into a cardiac tissue, such as an aortic annulus or a mitral annulus. The endothelial growth into these tissues can thus be increased, which leads to an improved ingrowth of the heart valve prosthesis provided with the sealing material. Due to the accelerated integration process, the healing process of the patient in question is accelerated, which results in an overall improved compatibility of a correspondingly equipped heart valve prosthesis and a greater acceptance of such a heart valve prosthesis as compared to the prostheses known from the prior art.

In a variant the hygroscopic matrix includes at least one substance having an anti-calcifying effect. This may be a hardness stabiliser, for example. Substances with an anti-calcifying effect can support an inhibition of a calcification or even a gradual regression of already existing calcifications. An example of such a substance with anti-calcifying effect is polysuccinimide. Already at a slightly elevated pH value, polysuccinimide is hydrolysed in part and is thus swellable in highly crosslinked form and water-soluble in linear form. Polyaspartic acid thus forms and is suitable as an inhibitor of inorganic calcifications, with long-lasting effect. Due to the introduction of such a substance with anti-calcifying effect into the hygroscopic matrix, or into the third component, the overall stability of the composite structure of the sealing material is not influenced, since the third component does not contribute substantially to the stability of the composite structure. If the new formation of calcifications can be effectively counteracted, or if existing calcifications can be broken down, the fatigue strength of an implant that is equipped with the sealing material claimed in accordance with the invention increases. Revision surgeries or valve-in-valve surgeries can thus be avoided. The acceptance of implants equipped in this way among relevant patients and surgeons thus increases.

In a variant the sealing material has a layered construction. The first component here forms a core region of the sealing material. The second component forms a first layer which surrounds the core region. The third component forms a second layer which surrounds the first layer. Consequently, with use of the sealing material, the third, rapidly swelling component comes firstly into contact with an aqueous solution and due to its rapid swelling can quickly provide a first sealing effect of the sealing material. The second, more slowly swelling component then comes into contact with the aqueous solution and can build up a longer-lasting and more stable sealing effect. Whether the first component comes into contact with an aqueous solution is irrelevant, since it retains its structural properties regardless of whether or not it is in contact with an aqueous solution. Due to its multi-layered construction, the advantageous properties of the sealing material can be provided in a particularly suitable way.

In a multi-layered construction of this kind the first component can be present for example in the form of a monofilament; that is to say in the form of a compact design. Alternatively, it is also possible that the first component is present as a multifilament, that is to say as an accumulation of numerous monofilaments arranged closely together. The first component is then typically less compact than in the case of a monofilament first component.

In an alternative embodiment the sealing material does not have a multi-layered construction. Rather, in this variant it has a multifilament construction, which consists of multiple (two or more) filaments of the first component, multiple filaments of the second component and multiple filaments of the third component, which are arranged regularly or irregularly relative to one another. A construction of this kind can also be referred to as a composite thread.

In a variant the second component or the hydrogel and the third component or the hygroscopic matrix are present in the form of a composite material. In this variant it is thus provided to blend the second component and the third component with one another in such a way that they ultimately act as an individual component for the macroscopic composition of the sealing material. This composite material formed of second component and third component then has a two-stage swelling behaviour; in other words it combines the above-described different swelling properties of the second component and the third component. The construction of macroscopic structures from a composite material of this kind can be simplified as compared to the use of three separate components. However, the swelling properties of the composite structure ultimately employed when using a composite material formed from second component and third component are less easily influenced or controlled.

A composite material of this kind can then be produced particularly easily in particular if a polymerisable ionic liquid is used as second component or in the second component and cellulose derivatives are used as third component or in the third component. This is because cellulose derivatives dissolve well in polymerisable ionic liquids, so that composite materials can be produced particularly easily. Diffusion barriers are thus broken down and the swelling time as a whole is further reduced. In the variants explained above or below, fibres or threads formed from a composite material of this kind can be used as fibres or threads formed from a single component.

In a variant the sealing material is present in the form of a monofilament thread, in the form of a multifilament thread, in the form of a cordage, in the form of a weft knit, in the form of a warp knit, in the form of a braiding and/or in the form of a nonwoven.

As already mentioned above, in the case of a monofilament thread, in particular the first component is formed as a monofilament polymer thread, whereas the second component and the third component are arranged in particular as a coating around this monofilament polymer thread. Here, the first component can be formed for example as a fibre with a diameter in the micrometre range to millimetre range and is subsequently coated step-by-step with the second component and the third component. Dipping, spraying or plasma polymerisation processes are suitable for this purpose, for example.

In the case of a multifilament thread, there are various possible embodiments of the composite structure. For example, merely the first component can be formed as a multifilament polymer thread, and once again—as also already explained above—can be coated by the second component and the third component. A multifilament polymer thread of this kind can be produced for example from an (electro)spun or extruded first component. The first component can then also be referred to as a core formed from spun staple fibres. A step-by-step coating with the second or third component is then performed. Dipping, spraying or plasma polymerisation processes are also suitable for this purpose, for example.

However, it is also possible that the individual components, considered in their own right, are present in the form of filaments, which together in a regular or irregular arrangement provide a multifilament thread. A multifilament thread of this kind can be produced for example from individual oriented polymer fibres or from oriented polymer fibres (electro)spun or extruded together. For this purpose, three separate nozzles for example can be used in order to spin or to extrude the three different components simultaneously. In a further process step, the three components spun or extruded in this way are then bundled/plied to form a multifilament thread (which can also be referred to as a yarn).

A further multifilament thread can be produced for example from a plurality of three-component fibres, for example by triaxially electrospun, oriented polymer fibres. These can be electrospun via a single, triaxially constructed nozzle and can be bundled/plied in a subsequent method step to form a multifilament thread (which can also be referred to as a yarn).

A cordage is a structure consisting of a plurality of threads, in which structure the individual threads engage around one another. An embodiment of the sealing material as a cordage makes it possible to use the properties of the individual components in a spatially resolved manner. This is of particular importance in particular if the sealing material is to be used as part of a medical implant, in particular for sealing a medical implant with respect to a mitral annulus. This is because particularly advantageous sealing properties of the sealing material can then be achieved by a corresponding spatial resolution.

A cordage can be realised as a plied/turned cordage. A cordage of this kind consists of monofilament strands of the first component, the second component and the third component and can be produced for example by extrusion or reshaping manufacturing methods. Equally, monofilament threads can also be used for a plied or turned cord of this kind, in which the three individual components are arranged as in the above-described monofilament thread (a monofilament core formed from the first component with a coating formed from the second component and the third component).

Lastly, a cord can also be produced from multifilament polymer threads, as have already been explained above.

A weft knit, a warp knit or a braiding can be produced from the above-explained threads, the above-explained cordage or combinations of the above-explained threads and the above-explained cordage.

A nonwoven, which can also be referred to as a nonwoven two-dimensional structure, has multiple non-oriented or oriented polymer fibres, in particular multiple monofilament, three-component polymer fibres. For example, it is possible to arrange a plurality of layers of directed polymer fibres above one another in order to produce a nonwoven structure of this kind.

In a variant a nonwoven of this kind has a porosity between 2 μm and 20 μm, in particular between 3 μm and 19 μm, in particular between 4 μm and 18 μm, in particular between 5 μm and 17 μm, in particular between 5 μm and 16 μm, in particular between 6 μm and 15 μm, in particular between 7 μm and 14 μm, in particular between 8 μm and 13 μm, in particular between 9 μm and 12 μm, in particular between 11 μm and 12 μm.

The combination of three components to form a composite structure opens up new possibilities for a rapid, controllable and strong swelling behaviour alongside improved mechanical stability of the entire structure. Here, it is possible in a variant to selectively adjust or adapt the swelling behaviour by external stimuli and by the arrangement of the individual components of the composite material. Equally, the possible delivery of active ingredients additionally contained in the individual components can be controlled selectively. Since the composite structure can be constructed in the form of threads, cordages, larger structures produced from fibres and/or cordages and/or from nonwovens, a broader field of application results than is the case for the sealing materials known from the prior art. In addition, texture-dependent properties, such as strength, stretchability, orientation of the sealing material, etc. can be better modulated and adapted to the particular requirements.

To summarise, the sealing material according to the invention represents a composite structure which
- can be used in various systems (for example threads/cordage/knitted fabric/areal structure);
- can be processed by conventional textile processing techniques to form specially conditioned and produced fabrics;
- can swell in a directed manner;
- can remain permanently in the body of a patient;

- allows a delayed delivery of active ingredients which are embedded in individual components of the composite structure;
- can deliver a growth factor for promoting the endothelialisation;
- can impart in particular a long-lasting anti-calcifying effect by the addition of appropriate substances such as hardness stabilisers;
- can fasten to a heart valve prosthesis, in particular to the stent structure of a heart valve prosthesis; and
- is suitable for sealing between a heart valve prosthesis, such as a transcatheter aortic valve prosthesis (TAVI, TAVR, PAVR) and a vessel wall of a patient, for example an aortic annulus.

One aspect of the present invention relates to a medical implant which includes a sealing material according to the above explanations. Here, this sealing material is arranged on at least a region of the surface of the implant. This region is a region that in the implanted state of the implant is intended and designed to contact a vessel of a patient in whom the medical implant has been implanted. It is thus possible that the sealing material will exert its sealing properties between the implanted medical implant and an anatomical structure of a patient, for example a vessel wall, where the implant has been implanted.

In a variant the medical implant is a vessel valve prosthesis, in particular a heart valve prosthesis. Here, an aortic valve prosthesis, a tricuspid valve prosthesis and a mitral valve prosthesis for example are suitable examples of a heart valve prosthesis. Such prostheses or implants typically have a stent-like structure, which in its interior carries a valve arrangement which replaces a natural vessel valve or heart valve. The sealing material here can be applied to the surface of the heart valve prosthesis or, for example, can be wound in the form of a thread or a cordage around individual portions of the stent structure of the medical implant.

In a variant the medical implant is an overall system that is stored dry and/or supplied dry, in particular it is a heart valve prosthesis that is stored dry/supplied dry. This is because as soon as the sealing material comes into contact with water or an aqueous liquid, such as blood, it starts to swell. Consequently, the sealing material is expediently stored and provided for the surgery in a dehydrated state, so that it only comes into contact with blood once it is in the body of a patient, whereby a swelling of the third component and of the second component is then initiated.

In a variant the heart valve prosthesis together with the sealing material is loaded in a dehydrated state into a so-called catheter-delivery system and is supplied in this preloaded state to an operating theatre.

All variants of the sealing material can be combined in any way with one another and can be transferred in any combination to the described medical implant, and vice versa.

FIG. 1 shows a monofilament thread formed from a sealing material which includes a first component 1, a second component 2 and a third component 3. The first component 1 includes a biologically inert polymer, which is spun into a individual polymer fibre. The fibre diameter typically lies in the micrometre to millimetre range. The second component 2 is applied to the first component 1 by dipping, spraying or plasma polymerisation processes. Similarly, the third component is applied to the second component 2 by dipping spraying or plasma polymerisation processes. This results in a layered construction, in which the first component 1 represents the core and the second component 2 and the third component 3 represent a coating.

The second component 2 includes a hydrogel here, which swells upon contact with an aqueous solution. The third component 3 has a hygroscopic matrix and likewise swells upon contact with an aqueous, but much more quickly than the second component 2. The monofilament polymer thread as per FIG. 1 thus has temporally staggered swelling properties.

Figure 2:
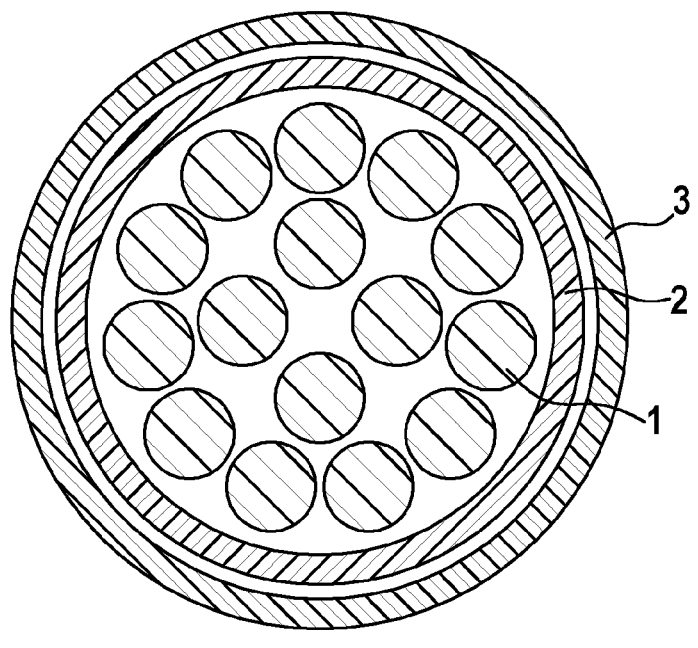
FIG. 2 a second exemplary embodiment of a thread formed from a sealing material.

FIG. 2 shows a multifilament polymer thread formed from the first component 1, the second component 2 and the third component 3. In this figure and in all subsequent figures, like elements are provided with like reference signs in each case. In addition, the first component 1, the second component 2 and the third component 3 in all exemplary embodiments have the composition explained in conjunction with FIG. 1, unless explicitly stated otherwise.

The first component 1 in the exemplary embodiment as per FIG. 2 is an electrospun or extruded thread which consists of individual fibres of the first component 1. This thread consisting of individual fibres and formed from the first component 1 is then coated step-by-step with the second component 2 and the third component 3. This can be achieved once again by a dipping, spraying or plasma polymerisation process, for example.

Figure 3:
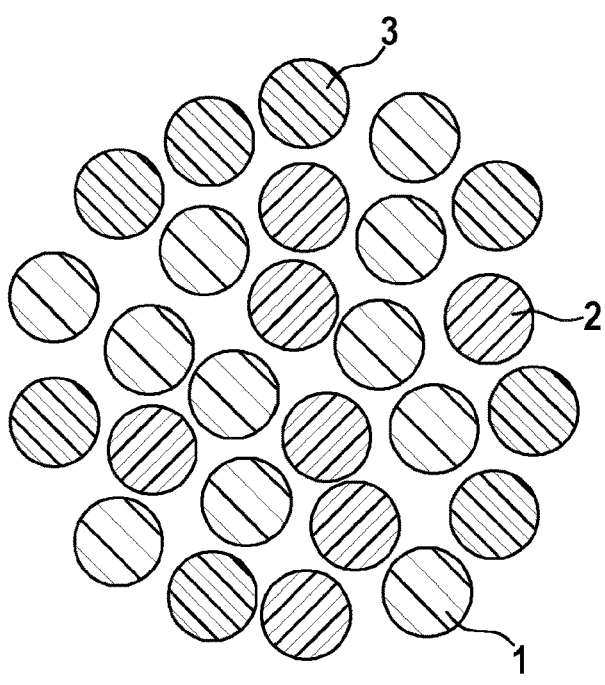
FIG. 3 a third exemplary embodiment of a thread formed from a sealing material.

FIG. 3 likewise shows the cross section of a multifilament polymer thread. Here, however, individual fibres of the first component 1, the second component 2 and the third component 3 are arranged irregularly relative to one another. A multifilament thread of this kind can be produced from individual oriented polymer fibres or from oriented polymer fibres spun or extruded together, by bundling or plying in a further method step the fibres formed from the first component 1, the fibres formed from the second component 2, and the fibres formed from the third component 3.

Figure 4:
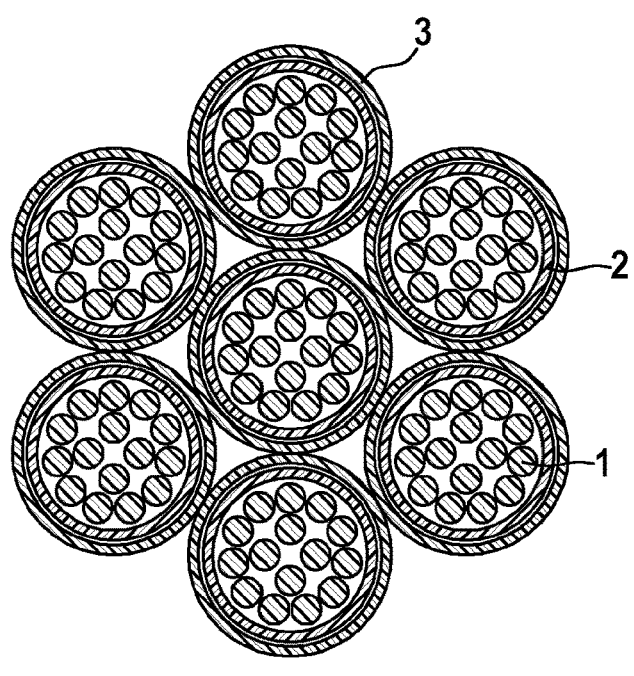
FIG. 4 a fourth exemplary embodiment of a thread formed from a sealing material.

FIG. 4 shows a further exemplary embodiment of a multifilament thread, in which the individual three-component threads, which each consist of the first component 1, the second component 2 and the third component 3, are bundled or plied to form a multifilament thread. The three-component threads can be electrospun via a single, triaxially constructed nozzle.

Figure 5:
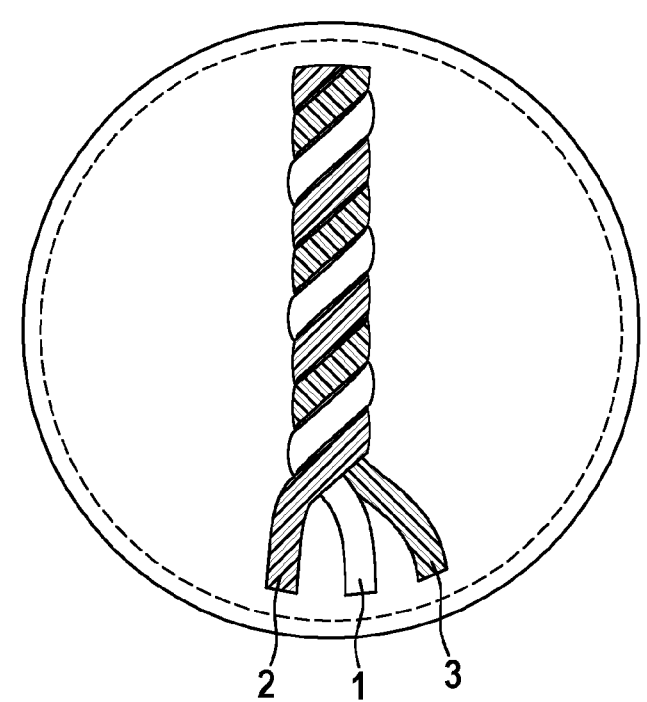
FIG. 5 an exemplary depiction of a cordage formed from a sealing material.

FIG. 5 shows a schematic view or a cordage consisting of individual strands of the first component 1, the second component 2 and the third component 3. In a cordage of this kind, the properties of the individual components are arranged in a spatially resolved manner. Possible structures of a cordage of this kind are described in greater detail in FIGS. 6 to 8.

Figure 6:
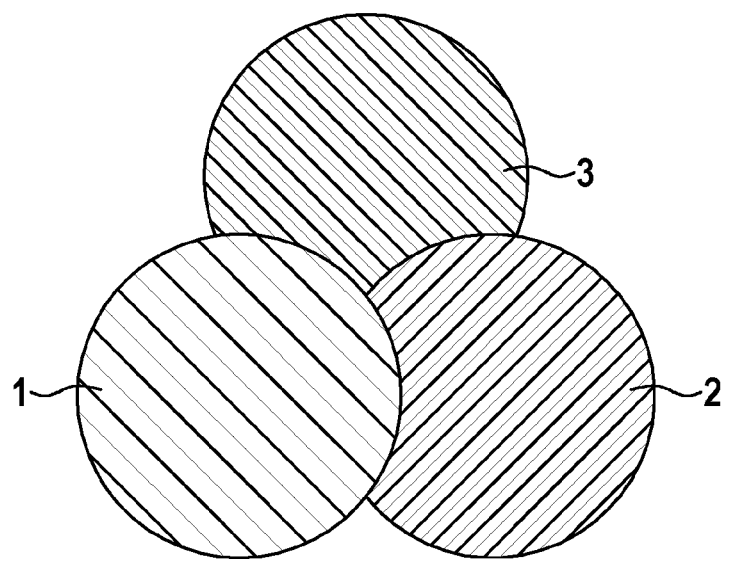
FIG. 6 a first exemplary embodiment of the construction of a cordage formed from a sealing material.

FIG. 6, for example, shows a cross section through a cordage in which individual strands of the first component 1, the second component 2 and the third component 3 are plied together or twisted against one another. A cord of this kind can be produced for example by extrusion or manufacturing methods in which the individual strands are reshaped.

Figure 7:
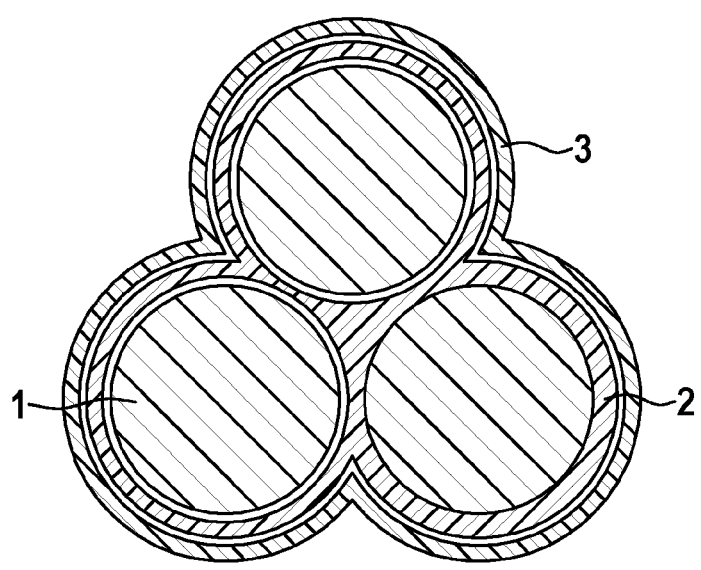
FIG. 7 a second exemplary embodiment of the construction of a cordage formed from a sealing material.

FIG. 7 shows a cord that consists of monofilament composite threads. Each of these composite threads includes the first component 1, the second component 2 and the third component 3. The construction of an individual composite thread of this kind is described in greater detail in FIG. 1. These individual composite threads are also plied with one another or twisted relative to one another.

Figure 8:
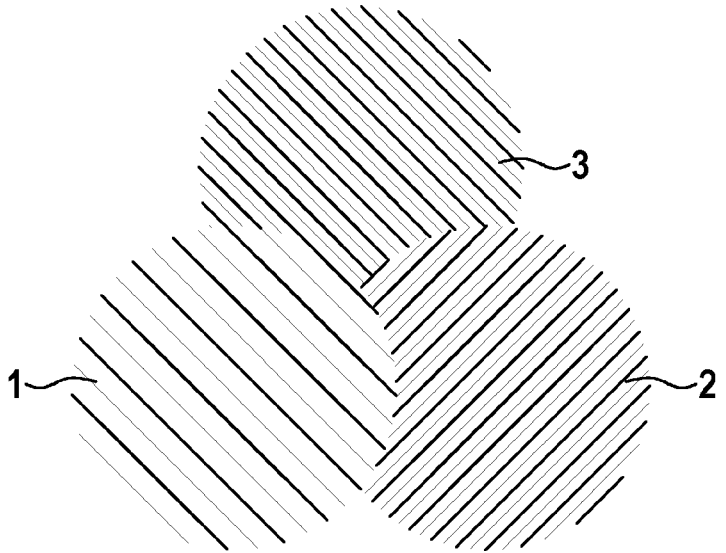
FIG. 8 a third exemplary embodiment of the construction of a cordage formed from a sealing material.

FIG. 8 shows the cross section through a cord formed from multifilament threads, which can be constructed in principle similarly to the threads shown in FIGS. 2, 3 and 4. In this case, the individual threads used for the cord of FIG. 8 are mono-component multifilament threads; they thus correspond in terms of their construction to the individual strands of the thread as per the exemplary embodiment from FIG. 3.

Figure 9A:
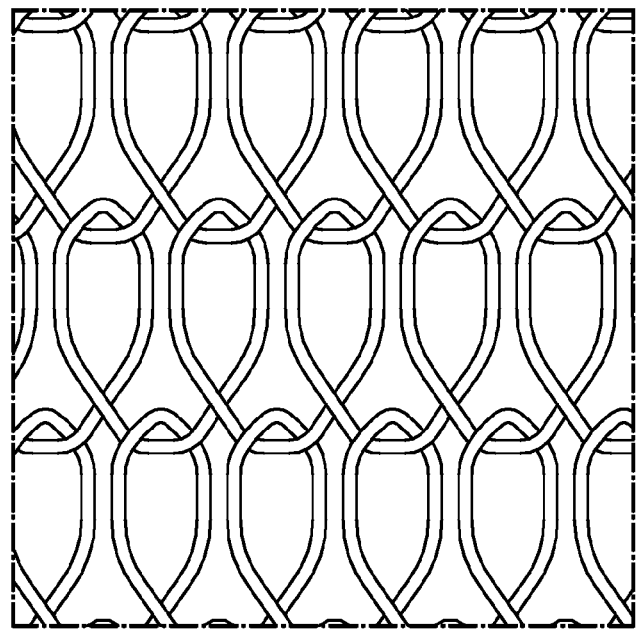
FIG. 9A an exemplary embodiment of a weft knit formed from a sealing material.

Two-dimensional structures can be produced from the different threads as per FIGS. 1 to 4 or the different cordages as per FIGS. 5 to 8 and are able to cover larger areas with the sealing material claimed in accordance with the invention. FIG. 9A shows a first exemplary embodiment of such a two-dimensional structure, specifically in the form of a weft knit fabric (also referred to as a weft knit). To produce such a weft knit fabric, individual threads or individual cordages or combinations of threads and cordages are knitted together.

Figure 9B:
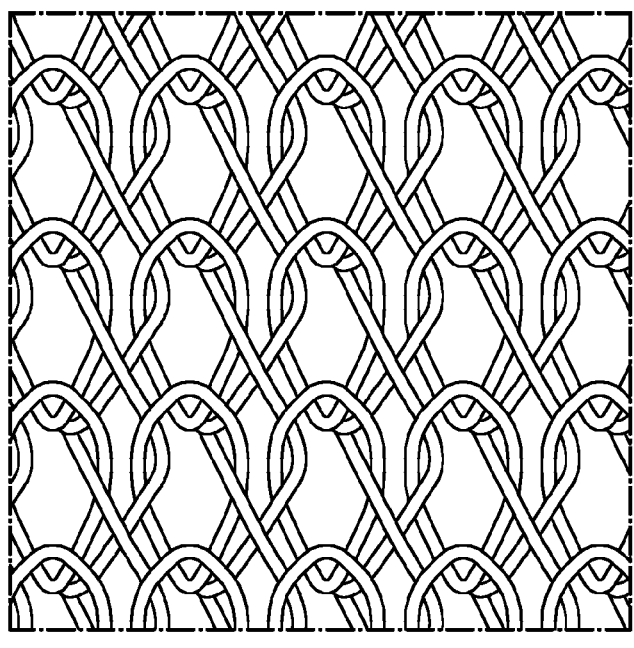
FIG. 9B an exemplary embodiment of a warp knit formed from a sealing material.

FIG. 9B shows a two-dimensional structure in the form of a warp knit. Here too, individual threads, individual cordages or combinations of threads and cordages can be knitted together.

Figure 9C:
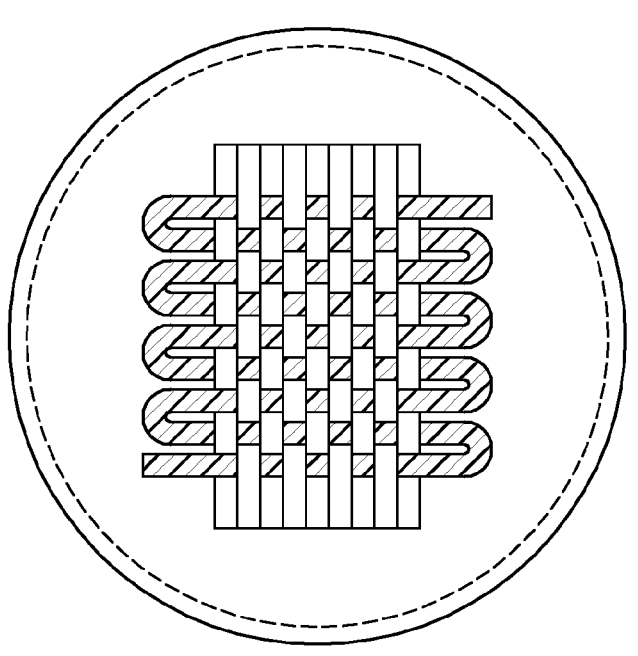
FIG. 9C an exemplary embodiment of a braiding formed from a sealing material.

FIG. 9C lastly shows a braiding (also referred to sometimes as a woven fabric) formed from individual threads or individual cordages or from a combination of threads and cordage. Consequently, the threads and the cordage can be processed from the sealing material according to conventional textile processing techniques to form different fabrics.

Figure 10:
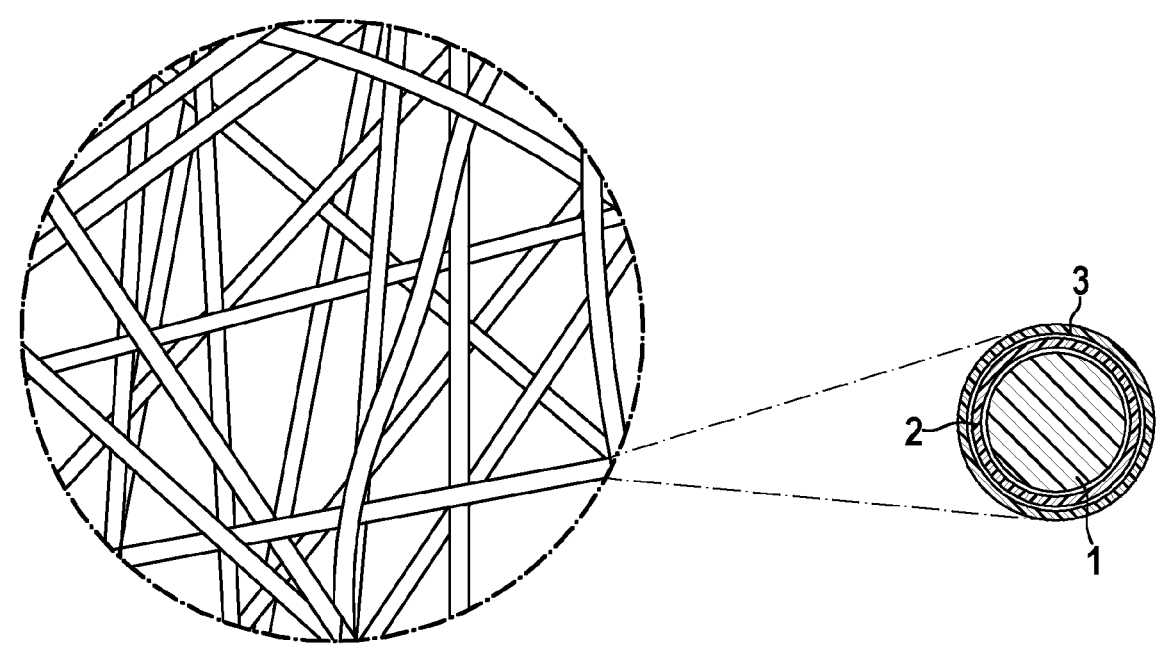
FIG. 10 an exemplary embodiment of a nonwoven formed from a sealing material.

FIG. 10 shows a further possible areal structure of the sealing material, specifically in the form of a nonwoven. A nonwoven of this kind consists of oriented or non-oriented three-component fibres, as described for example in FIG. 4. Triaxially electrospun polymer fibres of this kind can be deposited in non-oriented form or oriented in a plurality of layers, on a surface, in order to produce a nonwoven.

Figure 11A:
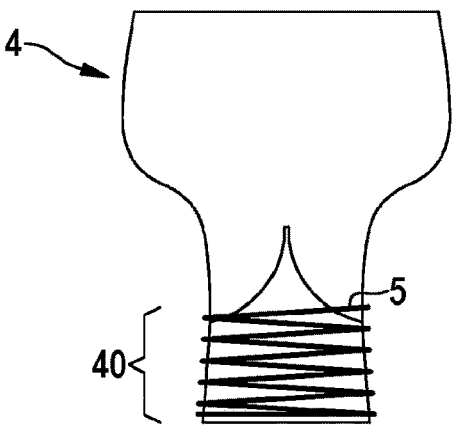
FIG. 11A a schematic depiction of a first exemplary embodiment of a heart valve prosthesis including a sealing material.

FIG. 11A shows a schematic side view of a heart valve prosthesis 4 which is provided at an inflow-side region 40 with a sealing material 5, which can be formed in accordance with the exemplary embodiments shown in FIGS. 1 to 8. The sealing material 5 thus has a three-component construction. Here, it is formed as a thread or as a cord and is wound on an outer side of the heart valve prosthesis 4 around a support structure of the heart valve prosthesis 4. This sealing material 5 is thus particularly well suited for sealing the heart valve prosthesis 4 with respect to a cardiac annulus of a patient in whom the heart valve prosthesis 4 is implanted.

Figure 11B:
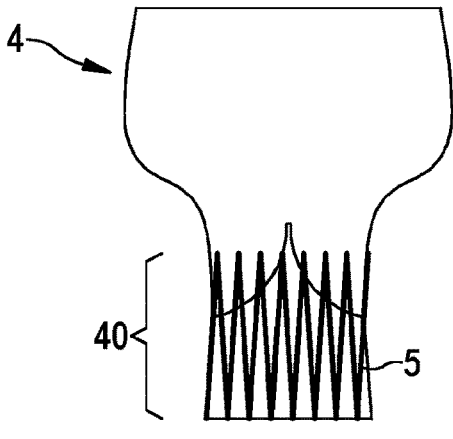
FIG. 11B a second exemplary embodiment of a heart valve prosthesis including a sealing material.

FIG. 11B shows a further exemplary embodiment of a heart valve prosthesis 4 which is provided at its inflow-side region 40 with a sealing material 5. In contrast to FIG. 11A, the sealing material 5 is not arranged here transversely to a direction of longitudinal extent of the heart valve prosthesis 4, but in a direction of longitudinal extent of the heart valve prosthesis 4. In this arrangement, the sealing material 5 is thus particularly well suited for sealing the heart valve prosthesis 4 with respect to a cardiac annulus of a patient in whom the heart valve prosthesis 4 has been implanted.

Figure 11C:
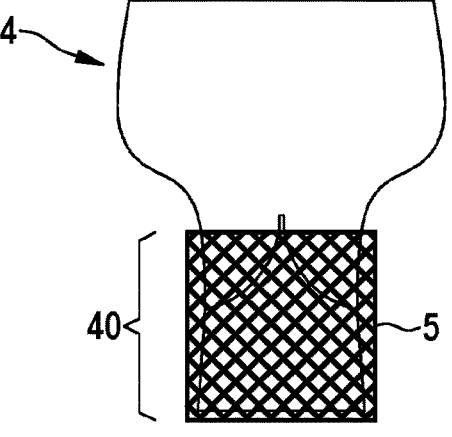
FIG. 11C a third exemplary embodiment of a heart valve prosthesis including a sealing material.

FIG. 11C shows a further exemplary embodiment of a heart valve prosthesis 4 in which a two-dimensional structure formed from a sealing material 5 is arranged at the inflow-side region 40. This two-dimensional structure can be, in particular, a weft knit, a warp knit, a braiding, or a nonwoven, as are shown by way of example in FIGS. 9A to 10. Due to the arrangement of the sealing material in the form of a two-dimensional material of this kind, in comparison to the exemplary embodiments shown in FIGS. 11A and 111B, an even larger region of the inflow-side region 40 of the heart valve prosthesis 4 is covered by the sealing material 5, so that on the whole an even stronger seal is produced between the heart valve prosthesis 4 and a vessel wall of a patient in whom the heart valve prosthesis 4 has been implanted, in particular with respect to a cardiac annulus of such a patient. The risk of a paravalvular leak can thus be reduced or avoided entirely. Due to the sealing material 5, there is a form fit towards the vessel wall of the patient, for example towards the aortic vessel wall of the patient.

Besides the exemplary embodiments shown in FIGS. 11A to 11C, in which the sealing material 5 is arranged externally on the heart valve prosthesis 4, it is also possible in principle to attach the sealing material between heart valve leaflets and a stent structure of the heart valve prosthesis 4. It is furthermore conceivable that the sealing material is braided through the individual cells of the stent structure of the heart valve prosthesis 4. The sealing material can also be filled for example into pockets that are formed on an outer side or an inner side of a stent structure of the heart valve prosthesis (for example by an inner apron or an outer apron which are attached to the stent structure). The contact of the sealing material with an aqueous liquid, such as blood, can then be temporally delayed, since the blood must first penetrate into the formed pockets in order to come into contact with the sealing material.

Figure 12A:
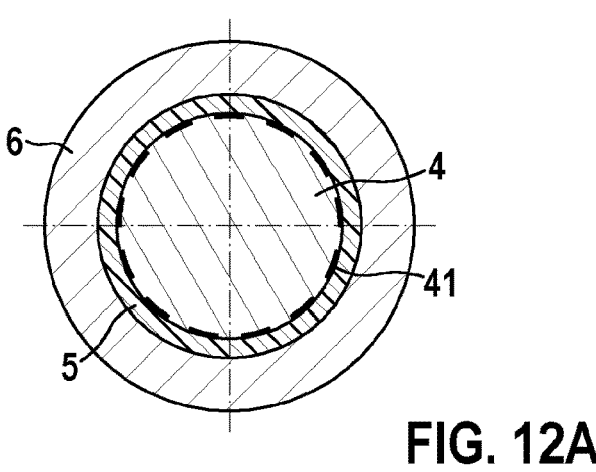
FIG. 12A a first schematic cross-sectional depiction of an aorta with implanted heart valve prosthesis.

FIG. 12A shows a schematic cross section through an aorta 6 into which a heart valve prosthesis 4 has been implanted. Here, the heart valve prosthesis 4 includes a stent structure 41, on the outer side of which the heart valve prosthesis 4 is provided with a sealing material 5. The sealing material—as explained above—is a three-composite material. FIG. 12A shows an ideal, round cross section of the aorta 6.

Figure 12B:
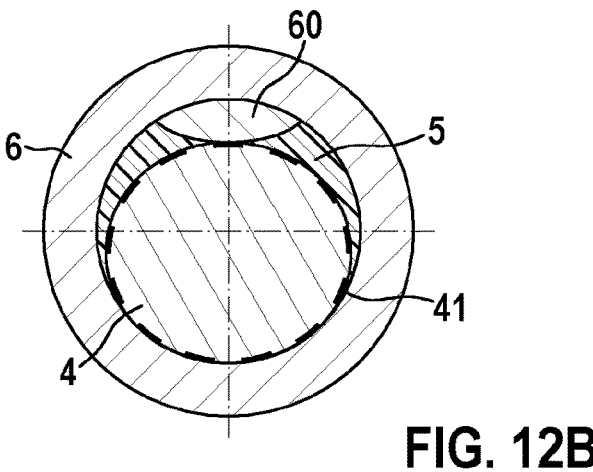
FIG. 12B a second schematic cross-sectional depiction of an aorta with implanted heart valve prosthesis.

By contrast, FIG. 12B shows the cross section through an aorta 6 which has a calcification 60. This results in the cross section in a non-uniformly implanted heart valve prosthesis 4 and a non-uniformly distributed sealing material 5. Nevertheless, the sealing material 5 is very well suited for sealing the heart valve prosthesis 4 with respect to the calcification 60 and thus ensuring a secure seating of the heart valve prosthesis 4 within the aorta 6.

Figure 12C:
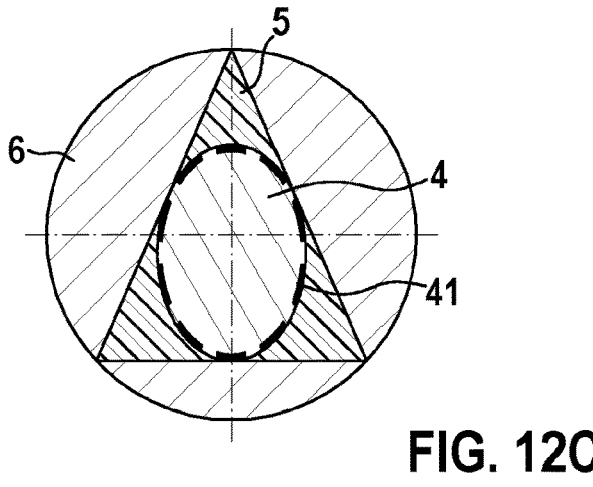
FIG. 12C a third schematic cross-sectional depiction of an aorta with implanted heart valve prosthesis.

FIG. 12C lastly shows a cross section through an aorta which has a substantially triangular cross section on account of valve cusps that have grown together. The heart valve prosthesis 4 is likewise implanted non-uniformly, wherein the sealing material 5 seals the remaining regions between heart valve prosthesis 4 and the aorta 6 in such a way that the heart valve prosthesis 4 is arranged securely in the aorta and no paravalvular leaks occur.

Consequently, the sealing material 5 is extremely well suited for sealing heart valve prostheses under different anatomical conditions and in the face of different anatomical challenges.

Figure 13A:
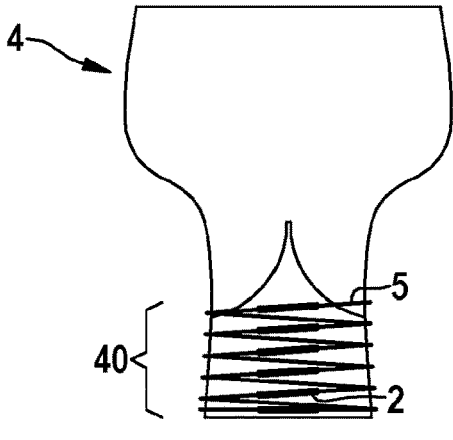
FIG. 13A a fourth exemplary embodiment of a heart valve prosthesis including a sealing material.

FIG. 13A shows a further schematic depiction of a heart valve prosthesis 4 which at its inflow-side region 40 has a sealing material 5. In this case, the sealing material 5 is designed in the form of a cordage, wherein the second component 2 of the sealing material 5 is provided in a spatially resolved manner at particularly relevant portions of the heart valve prosthesis 4 to a greater extent than in other portions of the heart valve prosthesis 4. The sealing material 5 in the exemplary embodiment as per FIG. 13A—similarly to the exemplary embodiment as per FIG. 11A—is arranged transversely to a direction of longitudinal extent of the heart valve prosthesis 4.

Figure 13B:
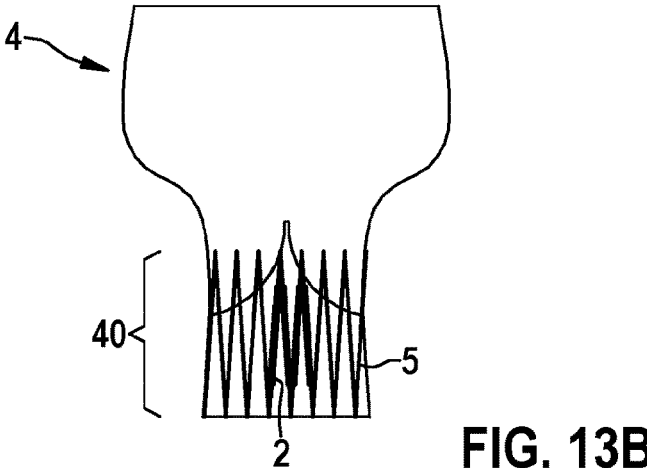
FIG. 13B a fifth exemplary embodiment of a heart valve prosthesis including a sealing material.

FIG. 13B shows a design of a heart valve prosthesis 4 comparable to FIG. 13A, wherein the sealing material 5—similarly to the exemplary embodiment as per FIG. 11B—is arranged on a direction of longitudinal extent of the heart valve prosthesis 4. Here, certain regions of the sealing material 5 have an elevated proportion of the second component 2 and thus, after appropriate contact with an aqueous solution, such as a bodily liquid, provide a strengthened seal in these regions between the heart valve prosthesis 4 and a vessel wall surrounding the heart valve prosthesis 4 in the implanted stated.

Figure 13C:
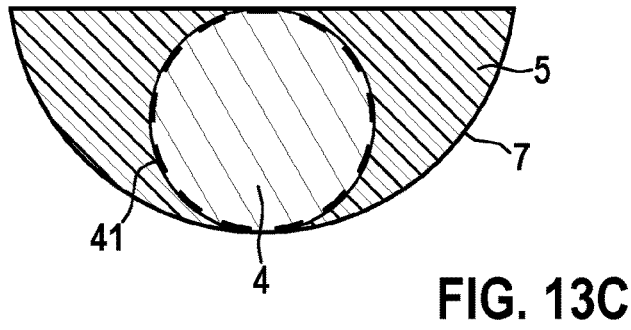
FIG. 13C a schematic view of a mitral annulus with implanted heart valve prosthesis.

FIG. 13C shows a schematic cross-sectional depiction through a mitral annulus into which a heart valve prosthesis 4 with a stent structure 41 has been inserted. Here, the stent structure 41 is surrounded by a sealing material 5 which reliably seals the heart valve prosthesis 4 with respect to the mitral annulus 7. The sealing material 5, which is part of the heart valve prosthesis 4, is for this purpose heavily swollen as compared to its starting state.

Figure 14:
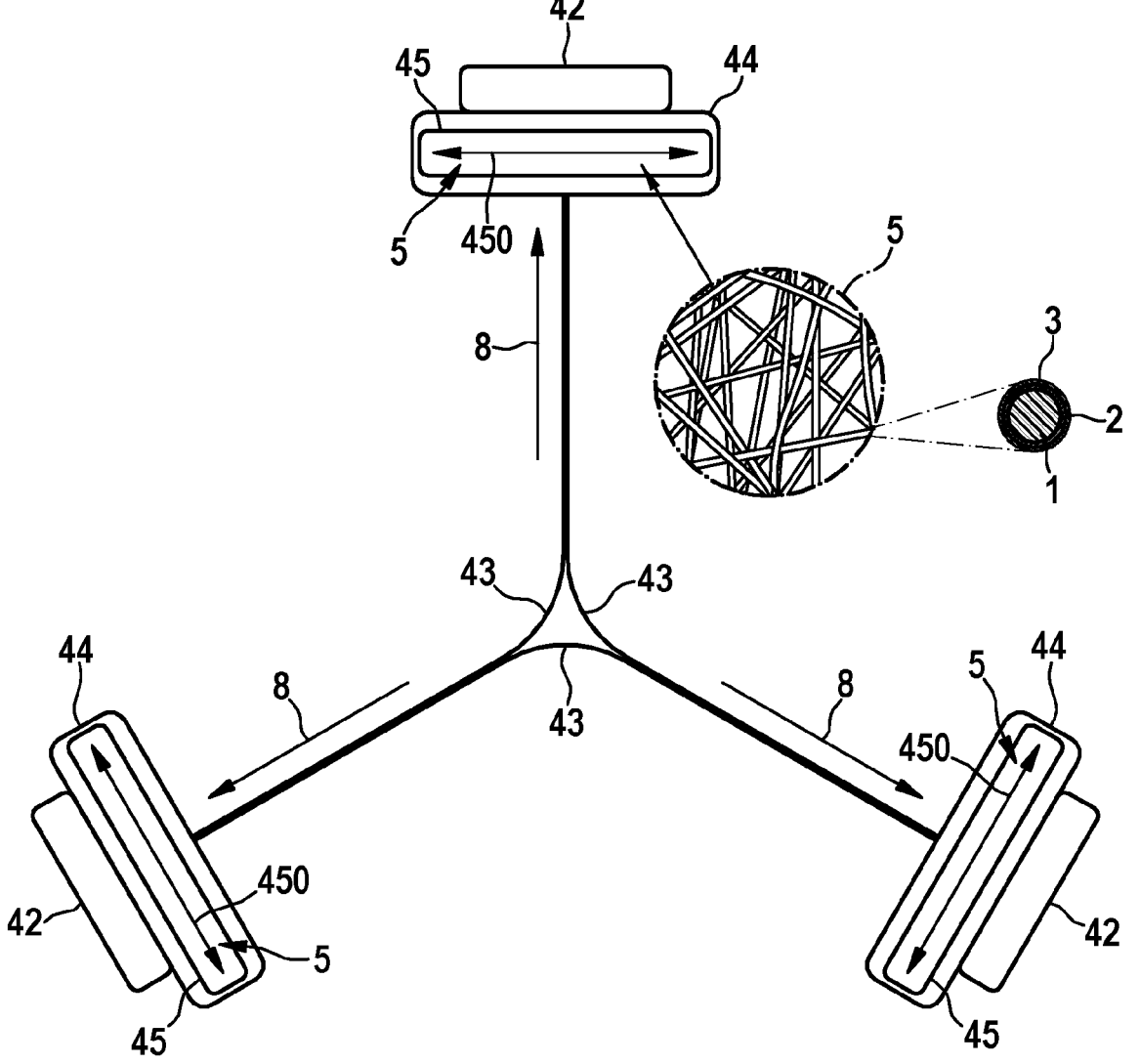
FIG. 14 a schematic depiction of the operating principle of the tightening of valve cusps with the aid of a sealing material.

FIG. 14 shows a schematic depiction of the operating principle of a tightening of valve cusps 43 of a heart valve prosthesis 4 by introducing sealing material 5 on a support structure of the heart valve prosthesis 4.

As explained above, heart valve prostheses 4 typically have a stent structure. Commissures 42 for fastening valve cusps 43 are routinely provided on this stent structure. In the exemplary embodiment of FIG. 14, the individual heart valve cusps 43 are fastened to the commissures 42 via outer pockets 44, which in their interior each have an inner pocket 45. These inner pockets 45 are filled with the three-component sealing material 5 in accordance with the above explanations. Here, the sealing material 5 is arranged in particular in the form of a swellable two-dimensional material—for example in the form of a nonwoven structure—in the inner pockets 45. As already explained in conjunction with FIGS. 1 to 10, the sealing material 5 consists of a first component 1, a second component 2 and a third component 3.

If the sealing material now comes into contact with a bodily liquid, in particular blood, or another aqueous liquid, the third component 3 swells first, and the second component 2 swells subsequently. Here, the inner pockets 45 are formed in such a way that they allow an expansion of the sealing material 5 in a direction of longitudinal extent 450, however an expansion transversely to this direction of longitudinal extent 450 is in essence prohibited.

As a result of this embodiment of the inner pockets 45, a swelling of the sealing material 5 is consequently accompanied by a tensile force 8 on the individual valve cusps 43, which acts in the direction of the commissures 42. The valve cusps 43 are thus tightened.

The sealing material 5 is therefore suitable not only for sealing a heart valve prosthesis with respect to a vessel wall surrounding the heart valve prosthesis, but can also be used for other purposes, for example for tightening heart valve cusps. In this regard, the temporally staggered swelling of the sealing material 5 also has a key advantage. This is because the forces exerted on the heart valve cusps 43 thus act in a temporally staggered manner. An initial loading of the heart valve cusps 43 can thus be reduced and an overall improved and more lasting tightening of the heart valve cusps 43 can be achieved.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. A sealing material for a medical implant, comprising a composite structure that comprises a first component, a second component and a third component, wherein the first component comprises at least one biologically inert polymer, the second component comprises a hydrogel, which swells up after contact with an aqueous solution by a first volume increase within a first time period, and the third component comprises a hygroscopic matrix, which swells up after contact with an aqueous solution by a second volume increase within a second time period, wherein the second time period is shorter than the first time period, wherein the first, second and third components each comprises a layer or thread that is separate from other ones of the first, second and third components, and wherein the sealing material has a layered construction, wherein the first component forms a core region of the sealing material, the second component forms a first layer which surrounds the core region, and the third component forms a second layer which surrounds the first layer.

2. The sealing material according to claim 1, wherein the at least one biologically inert polymer has a tensile strength of from 0.1 $N/mm^2$ to 20 $N/mm^2$ and/or an elongation at break of from 30% to 500%.

3. The sealing material according to claim 1, wherein the first time period is from 1 hour to 10 hours and/or the first volume increase causes an increase of an initial volume of the hydrogel by at least a factor of 2.

4. The sealing material according to claim 1, wherein the second time period is from 10 seconds to 59 minutes and/or the second volume increase causes an increase of an initial volume of the hygroscopic matrix by at least a factor of 2.

5. The sealing material according claim 1, wherein the hydrogel is selected such that the first volume increase is accelerated or increased by an external stimulus.

6. The sealing material according to claim 1, wherein the at least one biologically inert polymer is selected from the group consisting of polyurethanes, polyimides, polyethylenes, polypropylenes, polysulfones, polyesters, polytetrafluoroethylene, silicones, fluorosilicones, polyaryletherketones, polyvinylidene fluoride, vinylpyrrolidone/vinylacetate-copolymers and polyvinylfluoride.

7. The sealing material according to claim 1, wherein the hydrogel comprises at least one substance selected from the group consisting of polymerisable ionic liquids, thermosensitive polymers, polyacrylamides, polyoxazolines, polyvinylethers and polyethylene glycols.

8. The sealing material according to claim 1, wherein the hygroscopic matrix comprises at least one substance selected from the group consisting of cellulose matrix, cellulose derivatives and chitosan.

9. A sealing material for a medical implant, comprising a composite structure that comprises a first component, a second component and a third component, wherein the first component comprises at least one biologically inert polymer, the second component comprises a hydrogel, which swells up after contact with an aqueous solution by a first volume increase within a first time period, the third component comprises a hygroscopic matrix, which swells up after contact with an aqueous solution by a second volume increase within a second time period, wherein the second time period is shorter than the first time period, wherein the first, second and third components each comprises a layer or thread that is separate from other ones of the first, second and third components, and wherein the second component comprises at least one substance for promoting endothelialisation.

10. A sealing material for a medical implant, comprising a composite structure that comprises a first component, a second component and a third component, wherein the first component comprises at least one biologically inert polymer, the second component comprises a hydrogel, which swells up after contact with an aqueous solution by a first volume increase within a first time period, the third component comprises a hygroscopic matrix, which swells up after contact with an aqueous solution by a second volume increase within a second time period, wherein the second time period is shorter than the first time period, wherein the first, second and third components each comprises a layer or thread that is separate from other ones of the first, second and third components, and wherein the third component comprises at least one substance having an anti-calcifying effect.

11. The sealing material according to claim 10, wherein the sealing material has a layered construction, wherein the first component forms a core region of the sealing material, the second component forms a first layer which surrounds the core region, and the third component forms a second layer which surrounds the first layer.

12. The sealing material according to claim 1, wherein the second component and the third component comprise a composite material.

13. A sealing material for a medical implant, comprising a composite structure that comprises a first component, a second component and a third component, wherein the first component comprises at least one biologically inert polymer, the second component comprises a hydrogel, which swells up after contact with an aqueous solution by a first volume increase within a first time period, the third component comprises a hygroscopic matrix, which swells up after contact with an aqueous solution by a second volume increase within a second time period, wherein the second time period is shorter than the first time period, wherein the first, second and third components each comprises a layer or thread that is separate from other ones of the first, second and third components, and wherein the sealing material is in the form of a monofilament thread, a multifilament thread, a cordage, a weft knit, a warp knit, a braiding and/or a two-dimensional structure comprising multiple non-oriented or oriented fibres.

14. A medical implant, comprising a sealing material according to claim 1 in at least at one region of the surface of the medical implant, the sealing material being located on the implant to contact an anatomical structure of a patient when implanted.

15. The sealing material according to claim 1, wherein the hydrogel after the first volume increase has a tensile strength of from 0.02 $N/mm^2$ to 1 $N/mm^2$ and/or an elongation at break of from 30% to 130%.

16. The sealing material according to claim 1, wherein the hygroscopic matrix after the second volume increase has a tensile strength of up to 2.5 N/mm² and/or an elongation at break of from 10% to 40%.

17. The sealing material according to claim 1, wherein the at least one biologically inert polymer has a tensile strength of from 0.1 N/mm² to 20 N/mm² and an elongation at break of from 30% to 500%, the hydrogel after the first volume increase has a tensile strength of from 0.02 N/mm² to 1 N/mm² and an elongation at break of from 30% to 130%, and the hygroscopic matrix after the second volume increase has a tensile strength of up to 2.5 N/mm² and an elongation at break of from 10% to 40%.

18. The sealing material according to claim 1, wherein the third component comprises a spongy structure.

19. The sealing material according to claim 10, wherein the second component comprises at least one substance for promoting endothelialisation.

20. The sealing material according to claim 9, wherein the sealing material has a layered construction, wherein the first component forms a core region of the sealing material, the second component forms a first layer which surrounds the core region, and the third component forms a second layer which surrounds the first layer.

* * * * *